United States Patent [19]
DeLuca et al.

[11] Patent Number: 5,064,770
[45] Date of Patent: * Nov. 12, 1991

[54] ASSAY FOR 1,25-DIHYDROXY VITAMIN D RECEPTOR PROTEIN

[75] Inventors: Hector F. DeLuca, Deerfield; Maria E. Sandgren, Madison, both of Wis.

[73] Assignee: Wisconsin Alumni Research Foundation, Madison, Wis.

[*] Notice: The portion of the term of this patent subsequent to Mar. 28, 2006 has been disclaimed.

[21] Appl. No.: 388,203

[22] Filed: Aug. 1, 1989

[51] Int. Cl.$^5$ .................. G01N 33/536; G01N 33/566
[52] U.S. Cl. .................................... 436/542; 436/501; 436/536
[58] Field of Search ................................ 436/501, 542

[56] References Cited
U.S. PATENT DOCUMENTS 4,816,417  3/1989  DeLuca et al. ..................... 436/501

FOREIGN PATENT DOCUMENTS 238353  9/1987  European Pat. Off. .
302715  2/1989  European Pat. Off. .
322813  7/1989  European Pat. Off. .

OTHER PUBLICATIONS

M. Sandgren et al., 183 Anal. Biochem. 57-63 (Nov. 1989) (not prior art).
P. Milde et al., 37 J. Hist. Cyto. 1609-1617 (Nov. 1989) (not prior art).
M. Dame et al., 25 Biochem. 4523-4534 (1986).
E. Pierce et al., 261 Arch. Biochem. Biophys. 241-249 (1988).
E. Pierce et al., 153 Anal. Biochem. 67-74 (1986).
M. Dame et al., 82 P.N.A.S. U.S.A. 7825-7829 (1985).
T. Brown et al., 85 P.N.S.A. U.S.A. 2454-2458 (1988).
W. Wecksler et al., 92 Anal. Biochem. 314-323 (1979).
R. Shepard et al., 182 J. Biochem. 55-69 (1979).
S. Dokoh et al., 221 J. Biochem. 129-136 (1984).
J. Gershoni et al., 131 Anal. Biochem. 1-15 (1983).
D. Williams et al., 13 Biochem. 5537-5542 (1974).
G. Leclercq et al., 46 Can. Res. 4233s-4236s (1986).
S. Brailly et al., 116 J. Endocr. 427-434 (1988).
L. Miles et al., 219 Nature 186-189 (1968).
D. Hullet, Ph.D. Thesis, University Of Wisconsin-Madison 180-204 (1984).
A. Bolton et al., 133 J. Biochem. 529-539 (1973).
J. Kohn et al., 107 Biochem. Biophys. Res. Com. 878-884 (1982).
U. Laemmli, 27 Nature 680-685 (1970).
M. Bradford, 72 Anal. Biochem. 248-254 (1976).
J. Pike, 43 Nutri. Reviews 161-168 (1985).
Undated advertisement by Serono Diagnostics showing their magnetic antibody immuno assay system (admitted prior art).
J. Napoli et al., 19 Biochem. 2515-2521 (1980).

Primary Examiner—Wax, Robert A.
Assistant Examiner—Bradley Sisson
Attorney, Agent, or Firm—Quarles & Brady

[57] ABSTRACT

An immunoassay assay for 1,25-dihydroxy vitamin D receptor protein (3) is disclosed. It uses two antibodies (1) (7), one labelled (2) and one anchored with biotin (6). The two antibodies bind to different epitopes (4) (5) of the receptor (3) provided, and the biotin (6) permits use of avidin sepharose (8) to separate labelled receptor protein for measurement.

6 Claims, 3 Drawing Sheets

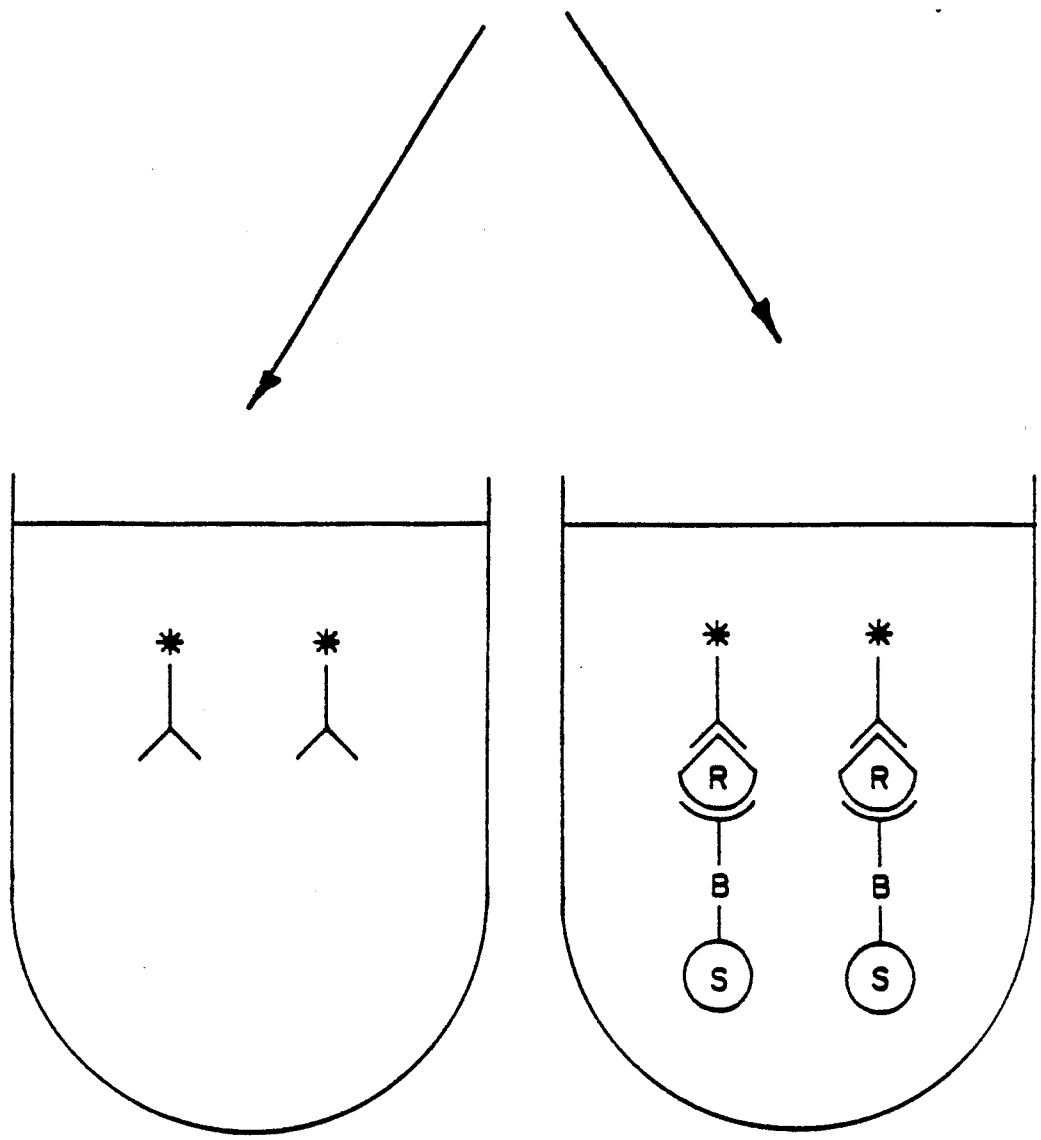
FIG. 4  FIG. 5

ASSAY FOR 1,25-DIHYDROXY VITAMIN D RECEPTOR PROTEIN

This invention was made with United States government support awarded by the National Institute of Health (NIH), Grant number DK-14881. The United States Government has certain rights in this invention This invention relates to an assay for testing for the level of 1,25-dihydroxy vitamin D receptor protein (e.g. in mammalian samples). More specifically it involves the use of immunoassay techniques as a diagnostic tool.

BACKGROUND OF THE INVENTION

Vitamin D is a well known vitamin which has many useful functions in mammals. It is activated by 25-hydroxylation in the liver and subsequently by 1-hydroxylation in the kidney. The active form of vitamin D, 1,25-dihydroxyvitamin $D_3$ ($1,25(OH)_2D_3$) regulates plasma calcium and phosphorus levels by acting on the intestine, bone and the kidneys. Other possible target organs include endocrine glands, skin, reproductive organs and the hematopoietic system.

Actions of the $1,25(OH)_2D_3$ hormone are believed to be mediated through an intracellular receptor protein to which it binds. See generally J. W. Pike, 43 Nutr. Rev. 161-168 (1985). The disclosure of this article and all other articles recited herein are incorporated by reference as if fully set forth herein. After binding of the hormone to the receptor protein, the receptor-hormone complex is thought to bind to specific DNA sequences and alter gene transcription.

Because of important known and proposed actions of vitamin D, it is of great interest to understand in a quantitative way the regulation, distribution, and turnover of its receptor protein. There is also reason to believe that the level of receptor protein will provide information as to the existence or stage of a disease, or its treatment (e.g. some cancers), and/or provide a means for monitoring and selecting drug treatments based on vitamin D variants.

Existing prior art techniques for assaying for vitamin D receptor rely on binding of radioactive vitamin D or on immunoblotting techniques. See generally W. Wecksler et al., 92 Anal. Biochem. 314-323 (1979); R. Shepard et al., 182 J. Biochem. 55-69 (1979); S. Dokoh et al., 221 J. Biochem. 129-136 (1984); and J. Gershoni et al., 131 Anal. Biochem. 1-15 (1983).

In a typical radioactive vitamin D assay, radiolabelled 1,25 vitamin D (the ligand) is added to the sample being tested. After binding, the bound complex is separated from unbound labelled 1,25 vitamin D with a compound called hydroxylapatite, and the radioactivity present in the bound fraction (and thus the receptor level) is measured. However, this technique measures only non-denatured forms of the receptor (and thus usually undercounts in an unpredictable manner), and may also in some cases be disrupted by the actions of vitamin D transport protein present in the sample.

Immunoblotting techniques use iodine labelled antibody. While they do measure denatured receptor, they provide only a crude approximation of vitamin $D_3$ receptor content.

Immunological assay using antibodies have been s successfully employed for certain other steroid hormone receptors such as estrogen and progesterone receptors. G. Leclecq et al., 46 Cancer Res. 4233-4236 (1986) and S. Brailly et al., 116 J. Endocrinol. 427-434 (1988). See also L. Miles et al., 219 Nature 186-189 (1968). Further, there is now available purified receptor protein (see T. Brown et al., 85 P.N.A.S. USA 2454-2458 (1988)) and monoclonal antibodies that bind to different epitopes on the receptor. M. Dame et al., 25 Biochem. 4523-34 (1986). However, to date no satisfactory radioimmunoassay has been developed for receptor protein that is sensitive, reproducible, easy to use, and useful in connection with crude samples from mammalian sources.

SUMMARY OF THE INVENTION

One aspect of the invention provides a binding assay to determine the amount of 1,25-dihydroxy vitamin D receptor in a sample. One adds to the sample a plurality of a first labelled antibody that is capable of binding at a first epitope on the receptor and a plurality of second antibody that is capable of binding at a second epitope on the receptor. Using means connectable to the second antibody, one then separates at least a portion of receptor protein that is bound to the labelled antibody from unbound labelled antibody. Thereafter, one measures the amount of labelled antibody present in on of the separated fractions.

In a preferred form, the separation step is performed using immunoprecipitation (e.g. a biotin/avidin sepharose system), the label is a radioactive label, and the fraction that is measured is the receptor bound fraction. The sample is preferably a human sample, but it may also come from animal sources or be part of a control experiment.

Kits for conducting such assays are also provided. They have a first radioactively labelled antibody capable of binding to a first epitope of the receptor protein and a second antibody capable of binding to a second epitope of the receptor protein. The second antibody can be biotinylated to render it readily immunoprecipitatable, and the first antibody can be radiolabelled with radioactive iodine (or other radioactive labels). In a preferred form, the kit also has 1,25-dihydroxy vitamin D receptor protein (to prepare a standard curve).

Thus, the invention focuses on the use of one labelled antibody and one anchorable antibody. They bind at different places on receptor protein, substantially without regard to denaturing. The "anchorable" antibody forms a means for the complex to be easily precipitated away from excess unbound labelled antibody (thus facilitating measurement).

It will be appreciated that in developing the present invention, the inventors had to overcome several problems. For one thing, vitamin D receptor protein is very unstable and will denature under many conditions. Also, tumor cell tissue will have varying degrees of vitamin D present, which will to varying degrees occupy the receptor. Further, techniques for anchoring the antibody in a way that produces reproducible results had to be developed. Other problems also had to be faced and overcome.

The objects of the invention therefore include:

(a) providing an assay of the above kind that is sensitive, reproducible, and easy to use;

(b) providing kits that are of assistance in performing assays of the above kind.

Still other objects and advantages of the present invention will be apparent from the description which follows.

DESCRIPTION OF THE DRAWINGS

FIG. 4 depicts unbound, labelled antibody that remains after the antibody-receptor complex has been separated out; and FIG. 5 depicts the antibody-receptor complex that has been separated from the residual, unbound, labelled antibody.

DESCRIPTION OF THE PREFERRED EMBODIMENTS

A. Buffers

Figure 1:
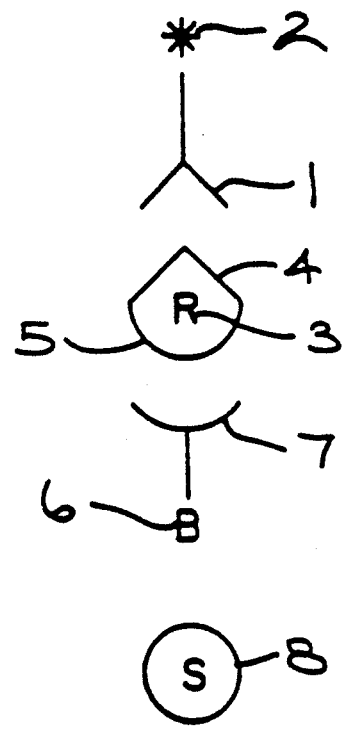
FIG. 1 identifies the key components of the assay of the present invention. It shows a first antibody(1), a radioactive iodine label(2) for the first antibody, 1,25(OH)$_2$D$_3$receptor (3), a first epitope(4) on the receptor, a second epitope(5) on the receptor, biotin(6), a second antibody(7), and avidinsepharose(8)
Figure 2:
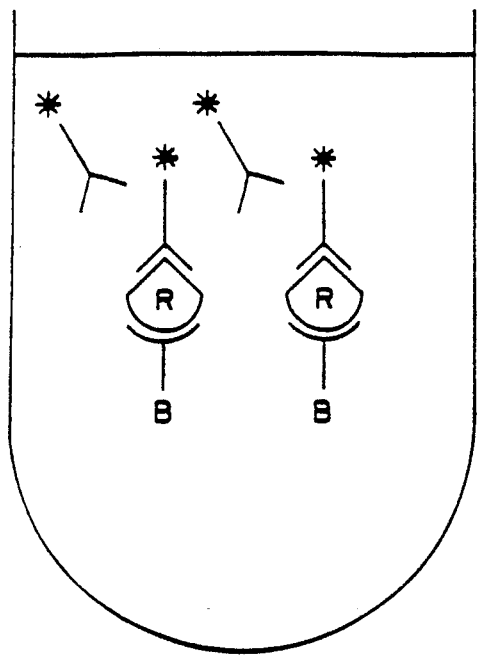
FIG. 2 depicts a first step in the preferred assay of the present invention where a supply of the labelled antibody is exposed to the first epitope of the receptor, and a biotin anchored antibody is exposed to the second epitope.
Figure 3:
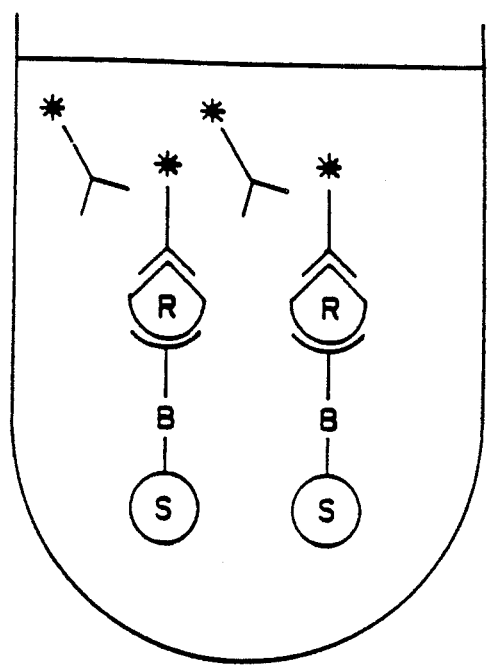
FIG. 3 depicts a separation step of the preferred assay where receptor that has bound to the two antibodies is immunoprecipitated with avidin-sepharose.

Phosphate-buffered saline (PBS), 1.5 mM KH$_2$PO$_4$/8.1 mM Na$_2$HPO$_4$ (pH 8.0)/137 mM KCl; PBS-Triton, 0.5% Triton X-100 in PBS; TE, 50 mM Tris-HCl (pH 7.4)/1.5 mM EDTA; TED, TE/5 mM dithiothreitol; TEDK 300, TED/300 mM KCl; TEDK 300–BSA, TEDK 300/0.5% (wt/vol) BSA/0.02% NaN$_3$.

B. Monoclonal Antibodies

A first antibody (1) and a second antibody (7), IVG8C11 and VD2F12, were generated to the porcine intestinal 1,25(OH)$_2$D$_3$ receptor (3) using the techniques described in M. Dame et al., 25 Biochem. 4523–34 (1986). Hybridomas capable of producing such antibodies can then be conveniently prepared as described by Dame et al., 25 Biochemistry 4523-34 (1986). Furthermore, a method for determining antibodies that bind to different epitopes (4)(5) is provided in this article. The antibodies produced by the hybridomas can be produced in mouse ascites and purified by chromatography on goat anti-mouse IgG-Sepharose (HyClone, Logan, Ut.). Both antibodies cross-react with receptor from a variety of species, including human. Purified antibody can be concentrated on an Amicon Ultrafiltration Cell and stored at −20° C.

C. Biotinylation Of Antibody VD2F12

Purified VD2F12 (7) was coupled with biotin (6) using N-hydroxysuccinimidobiotin (Sigma, St. Louis, Mo.), 0.1 M in N,N-dimethylformamide (Aldrich, Milwaukee, Wis.), 10 μl/mg antibody, for 1 hour at room temperature followed by extensive dialysis with phosphate buffered saline (PBS). For general biotinylation techniques, see D. Hullet, Ph.D. Thesis, University Of Wisconsin-Madison 180–204 (1984). D. Iodination Of Antibody IVG8C11.

Purified IVG8C11 (1), 5 μg in 10 μl PBS, was reacted with 1.0 mCi $^{125}$I (2) Bolton-Hunter Reagent (DuPont/NEN, Wilmington, Del.) for 2 hours on ice. See A. Bolton et al., 133 J. Biochem. 529–533 (1973) for general iodination techniques. The reaction was stopped with 0.25 ml 0.2 M glycine in 0.1 M borate (pH 8.5), for 5 minutes followed by addition of 0.25 ml PBS +0.25% (wt/vol) gelatin. The (Pharmacia, Uppsala, Sweden) saturated with BSA and preequilibrated with PBS+0.25% gelatin, to separate antibody bound from free $^{125}$I. Antibody preparations had a specific activity of 5–10 μCi/μg.

E. Preparation Of Avidin-Sepharose

Avidin from egg white (Calbiochem, San Diego, Calif.) was coupled to Sepharose CL 4B (Pharmacia, Uppsala, Sweden) at a concentration of 0.5 mg avidin per ml wet Sepharose, using the general cyanogenbromide activation procedure of Kohn et al., 107 Biochem. Biophys. Res. Commun. 878–884 (1982).

F. Preparation Of Pig Nuclear Exact (PNE)

To create one mammalian test sample, a high salt, crude nuclear extract from pig intestinal mucosa was obtained as previously described. See M. Dame et al., 82 P.N.A.S. USA 7825–29 (1985).

G. Cytosol Preparation

Weanling rats were obtained from the Holtzman Co. (Madison, Wis.) and kept on a diet containing 0.47% calcium, 0.30% phosphorus and no vitamin D. Intestinal whole cell extracts were prepared from 12-week-old rats as previously described. E. Pierce et al., 261 Arch. Biochem. Biophys. 241–49 (1988).

Biopsies of human duodenal mucosa from normal female volunteers (premenopausal) were obtained from the Mayo Clinic (Rochester, MN). Intestinal mucosal extracts were prepared using the same protocol as for rat intestinal mucosa. See generally A. Bolton et al., 133 J. Biochem. 529–39 (1973).

In the alternative, human tissue samples can be minced with a razor blade on ice, and washed by centrifugation (800×g) 4 times with TENa 150+1 mM DTT. After weighing, the tissue can be homogenized on ice by a glass-teflon system or polytron (depending on source) in 2 volumes of TEK$_{300}$+5 mM DTT+5 mM DFP. They are then ultracentrifuged 1 hour at 170,000×g. Supernatants are saved at −70° C. until use.

H. Preparation Of Purified 1,25-(OH)$_2$D$_3$ Receptor

Pig nuclear extract was subjected to immunoaffinity chromatography (T. Brown et al., 85 P.N.A.S. USA 2454–58 (1988)) and sodium dodecyl sulfate (SDS) polyacrylamide gel electrophoresis (U. Laemmli, 227 Nature 680–85 (1970)), and electroelution The purified receptor protein concentration was then determined by soft laser scanning densitometry (model SL-504-XL) (Biomed Instruments, Fullerton, Calif.) of a single 55 kDa band on Coomassie Blue stained SDS-polyacrylamide gels using ovalbumin, bovine serum albumin and carbonic anhydrase as standards (Sigma, St. Louis, Mo.). Purified receptor (3) was stored in aliquots at −70° C.

I. Protein Determination

Protein was determined by the technique of M. Bradford, 72 Anal. Biochem. 248–254 (1976) using bovine serum albumin as a standard.

J. Vitamin D Compounds

Radioactive 1,25-(OH)$_2$-[26,27-$^3$H]D$_3$ (160 Ci/mmol, 1 Ci=37 GBq) (for purposes of running a prior art assay for comparison) was produced by DuPont/NEN and prepared as previously described. J. Napoli et al., 19 Biochemistry 2515-2521 (1980). Nonradioactive 1,25-$(OH)_2D_3$ was a gift from the Hoffmann-La Roche Company.

THE ASSAY

For our reagents we used biotinylated antibody at 20 μg/ml (25 μL=0.5μg per tube); iodinated antibody −1.4×10⁶ cpm/ml (25 μL=35000 cpm per tube); and then the test or the standard sample.

The receptor standard was prepared as follows (1500 μL of 0.5 fmol/μL=750 fmol total). We made standards in 2.5 fmol increments by taking 20/40/60 . . . . 200 μL of concentrated standard (0.5 fmol/μL) in a total of 400 μL. Test samples can be diluted as desired and preferably 100 μL is used per assay tube. It is recommended to start at 1× with unknown samples, and dilute to 1:8 as required.

For example, biotinylated VD2F12 (0.5 μg) (6)(7) was incubated with iodinated IVG8C11 (40,000 cpm) (1)(2) and purified receptor standard (0-25 fmol) (3) (or alternatively a sample) for 16 hours at +4° C. in Beckman minitubes (Beckman, Palo Alto, Calif.). Assay buffer for this example was TEDK 300 +0.5% BSA and incubation volume 150 μl. Next a 50% slurry of avidin-Sepharose (8) in TE was added and incubated for 1 hour on ice (100 μl) with mixing every 20 minutes. The tubes were centrifuged at 800×g for 5 minutes. The resulting pellets were washed three times with PBS-Triton and counted in Packard Multi-Prias Auto-Gamma counter (Packard Instruments, Downers Grove, Ill.) Nonspecific binding (i.e. incubation mixture without receptor) was subtracted from all sample values.

For comparison, control tests were also run on samples using prior art techniques. In this regard, a modified (M. Dame et al., 82 P.N.A.S. USA 7825-29 (1985)) hydroxylapatite binding assay (D. Williams et al., 13 Biochemistry 5537-42 (1974); W. Wecksler et al., 92 Anal. Biochem. 314-23 (1979)) was used to determine the 1,25-$(OH)_2$-[26,27-³H]$D_3$ binding activity in samples. Pellets were counted in BioSafe II counting solution (RPI, Mount Prospect, Ill.) in a Prias 400 CL/D liquid scintillation counter (Packard Instruments, Downers Gove, Ill.).

In an especially preferred form, the assay is run over a two day period as follows:

DAY I

1. Start by adding the biotinylated antibody to the minitubes with a repeat pipetter (25 μL/tube).
2. Add iodinated antibody to each tube with a repeat pipetter (25 μL/tube).
3. Add receptor standard (or samples) to yield a total volume of 150 μL.
4. Mix tubes and cover with parafilm.

DAY II

6. Add avidin-Sepharose 100 μL of a 50% slurry.
7. Incubate on ice for 1 hour. Mix tubes every 15 minutes.
8. Wash pellets 3 times with PBS - 0.5% Triton X-100 by centrifugation at 800×g for 5 minutes.
9. The radioactivity of the pellets is counted in gamma-counter.

RESULTS

Purified 1,25-$(OH)_2D_3$ receptor (3) from pig intestinal mucosa was used as a receptor standard to create a standard curve (e.g. "X" level of radioactivity equals "Y" level of receptor).

The biotin linked antibody and the iodinated antibody are incubated simultaneously with increasing concentrations of receptor standard or sample followed by precipitation with avidin-Sepharose. After testing different receptor concentrations, a standard curve range of 0-25 fmol was found to give maximum sensitivity without excessive use of reagents. To determine the amount of iodinated antibody to be added to each assay tube, standard curves were obtained where radioactivity added ranged from 10,000 cpm to 100,000 cpm per tube. One hundred thousand cpm was found to be saturating. Since non-saturating amounts of iodinated antibody produced an excellent linear standard curve, routine use of 40,000 cpm was found to give low background (<10%) and high sensitivity. Concentrations of biotinylated antibody and avidin-Sepharose were carefully titrated and used at saturation. Usually 100 μL of a 50% slurry per tube was enough. The two antibodies used could be interchanged without altering assay results.

Since vitamin D hormone concentration (and thus receptor occupancy with vitamin D) varies in different tissues and preparations, the possibility that occupancy might affect receptor measurement was tested. Concentrations of receptor in samples of PNE were determined in the presence or absence of 4 nM 1,25-$(OH)_2D_3$. Data obtained show no significant difference between samples with or without hormone.

The present test finds greatest utility in samples other than PNE. For example, intestinal cyrosol from vitamin D-deficient rats and normal humans was prepared as described above and receptor content measured by the present assay and by the prior art ligand binding assay. Vitamin D-deficient rat intestinal extracts and human intestinal extracts, respectively, were found to have 2-fold and 5-fold higher receptor content by the present test than by ligand binding assay. In addition, variability was markedly lower with the immunoradiometric assay. We have also successfully used the test to measure receptor levels in rat kidney, chick intestine, chorioallantoic membrane from quail, a pig kidney cell line (LLC-$PK_1$), a human promyelocytic leukemia cell line (HL-60) and human breast cancers.

On rare occasion, the present test has given values somewhat lower than by ligand binding methods. We believe this is because of the presence of plasma vitamin D transport protein in the sample that produces a falsely high value by the ligand binding assay. This illustrates another disadvantage of ligand binding assay and advantage of the present invention.

It is believed that the present invention can provide important new information relating to the 1,25-$(OH)_2D_3$ receptor. For example, the receptor has been reported to be up-regulated and down-regulated in response to hormone, and likely regulated by age, glucocorticoid, and during development. Also, a receptor mediated anti-cancerous effect of vitamin D appears to exist in different human cell lines in vitro. If vitamin D related compounds are, in fact, used to treat malignancy, the present invention may be used to determine which cancers possess receptor in preparation for therapy. In this regard, immunoassays to measure estrogen and progesterone receptors are already widely used to predict the response to hormone treatment and to establish a prognosis in breast cancer patients.

It will be appreciated that the above description merely represents the preferred embodiments of the invention. The generic idea is to have two antibodies (1)(7) acting at two different epitopes (4)(5), one labelled (2), and the other anchorable (6) for easy separation. While radioactive labels are preferred, color (e.g. a peroxidase system), fluorescent, and enzyme (e.g. alkaline phosphatase) labels are also possible. The anchored antibody can also instead be attached to other types of beads, plastics, or particles, albeit the biotin system is highly preferred. For example, one might try adapting a magnetic particle system where the particle is anchored to one antibody (c.f. Serono Diagnostics of Randolph, Mass. which sells one type of magnetic anchoring system under the name "Prolactin MAIA" where precipitation is caused by a magnet). Further, the specific antibodies discussed are merely two of many possible antibodies. Thus, the claims should be looked to to assess the full scope of the invention.

We claim:

1. A binding assay to determine the amount of 1,25-dihydroxy vitamin D receptor in a sample that also has vitamin D transport protein in it, comprising the steps of:

adding to the sample a plurality of a first antibody that is capable of binding at a first epitope on vitamin D receptor protein, a plurality of a second antibody that is capable of binding at a second epitope on vitamin D receptor protein, and also a plurality of a label, such that the sample then has in it a complex of the receptor protein bound to the first antibody, the second antibody, and also the label, and such that the sample also has in it unbound label apart from the complex;

then, using means connectable to the second antibody, separating at least a portion of receptor protein bound to label from unbound label; and then, measuring the amount of label present in one of the separated fractions;

wherein the separation step is performed using immunoprecipitation.

2. The assay of claim 1, wherein the label is a radioactive label and at least one of the plurality of label is bound to the second antibody when the receptor is bound to a label.

3. The assay of claim 2, wherein the fraction measured is the receptor bound fraction.

4. A kit for conducting an assay for 1,25-dihydroxy vitamin D receptor protein, wherein the assay is a binding assay to determine the amount of 1,25-dihydroxy vitamin D receptor protein in a sample that also has vitamin D transport protein in it, the assay comprising the steps of:

adding to the sample a plurality of a first antibody that is capable of binding at a first epitope on vitamin D receptor protein, a plurality of a second antibody that is capable of binding at a second epitope on vitamin D receptor protein, and also a plurality of a label, such that the sample then has in it a complex of the receptor protein bound to the first antibody, the second antibody, and also the label, and such that the sample also has in it unbound label apart from the complex;

then, using means connectable to the second antibody, separating at least a portion of receptor protein bound to label from unbound label; and then, measuring the amount of label present in one of the separated fractions;

wherein the separation step is performed using immunoprecipitation;

said kit comprising:

a first radioactively labelled antibody capable of binding to a first epitope of vitamin D receptor protein; and a second antibody capable of binding to a second epitope of the receptor protein.

5. The kit of claim 4, wherein the second antibody is biotinylated.

6. The kit of claim 5, wherein the kit also has 1,25-dihydroxy vitamin D receptor protein.

* * * * *

UNITED STATES PATENT AND TRADEMARK OFFICE
CERTIFICATE OF CORRECTION

PATENT NO. : 5,064,770

DATED : November 12, 1991

INVENTOR(S) : Hector F. DeLuca, et al.

It is certified that error appears in the above-identified patent and that said Letters Patent is hereby corrected as shown below:

| | |
|---|---|
| Column 1, Line 65 | the extra "s" at the beginning of the line should be deleted. |
| Column 2, Line 24 | "present in on" should read "present in one" |
| Column 3, Line 61 | "D." should start on a new line as a section heading. |
| Column 4, Line 2 | After "The" add --mixture was then passed over a G-25 Sephadex column-- |
| Column 5, Line 10 | "-" should be "~" |
| Column 5, Line 63 | "15" should read -- 15-20 -- |

Signed and Sealed this

Ninth Day of March, 1993

Attest:

STEPHEN G. KUNIN

*Attesting Officer*   Acting Commissioner of Patents and Trademarks